United States Patent [19]

Nagy et al.

[11] Patent Number: 5,047,230
[45] Date of Patent: Sep. 10, 1991

[54] AEROSOL COMPOSITION COMPRISING NITROGLYCERIN AS ACTIVE INGREDIENT

[75] Inventors: Margit Nagy; József Kenderfi; Frigyes Görgényi; Margit Csörgö; Lidia Fedina, all of Budapest; Antal Mosonyi; Sándor Vajas, both of Körmend; Attila Mándi, Budapest, all of Hungary

[73] Assignee: EGIS Gyogyszergyar, Budapest, Hungary

[21] Appl. No.: 376,678

[22] Filed: Jul. 7, 1989

[30] Foreign Application Priority Data

Jul. 8, 1988 [HU] Hungary .............................. 3585/88

[51] Int. Cl.$^5$ ................................................ A61L 9/04
[52] U.S. Cl. ........................................ 424/45; 424/47
[58] Field of Search ................................ 424/45, 47

[56] References Cited

U.S. PATENT DOCUMENTS

| 4,001,391 | 1/1977 | Feinstone et al. | 424/47 |
| 4,369,173 | 1/1983 | Causland et al. | 424/47 |
| 4,440,777 | 4/1984 | Zupan | 424/274 |
| 4,482,534 | 11/1984 | Blank | 514/969 |
| 4,533,540 | 8/1985 | Blank | 514/970 |
| 4,885,173 | 12/1989 | Stanley et al. | 424/439 |
| 4,919,919 | 4/1990 | Aouda et al. | 424/45 |

Primary Examiner—Thurman K. Page
Assistant Examiner—P. L. Prater
Attorney, Agent, or Firm—Keil & Weinkauf

[57] ABSTRACT

The present invention relates to an aerosol composition free of propellant gas, comprising nitroglycerin as active ingredient. The composition according to the invention is composed of:

0.1 to 4% by weight of nitroglycerin,
51 to 90% by weight of a $C_{2-4}$ aliphatic alcohol (component A),
10 to 49% by weight of a polyalkyleneglycol comprising 2 or 3 carbon atoms in the alkylene moiety (component $B_1$) and/or a $C_{2-8}$ alcohol comprising two or three hydroxy groups (component $B_2$)

optionally together with one or more pharmaceutically acceptable carriers and/or diluents.

13 Claims, 1 Drawing Sheet

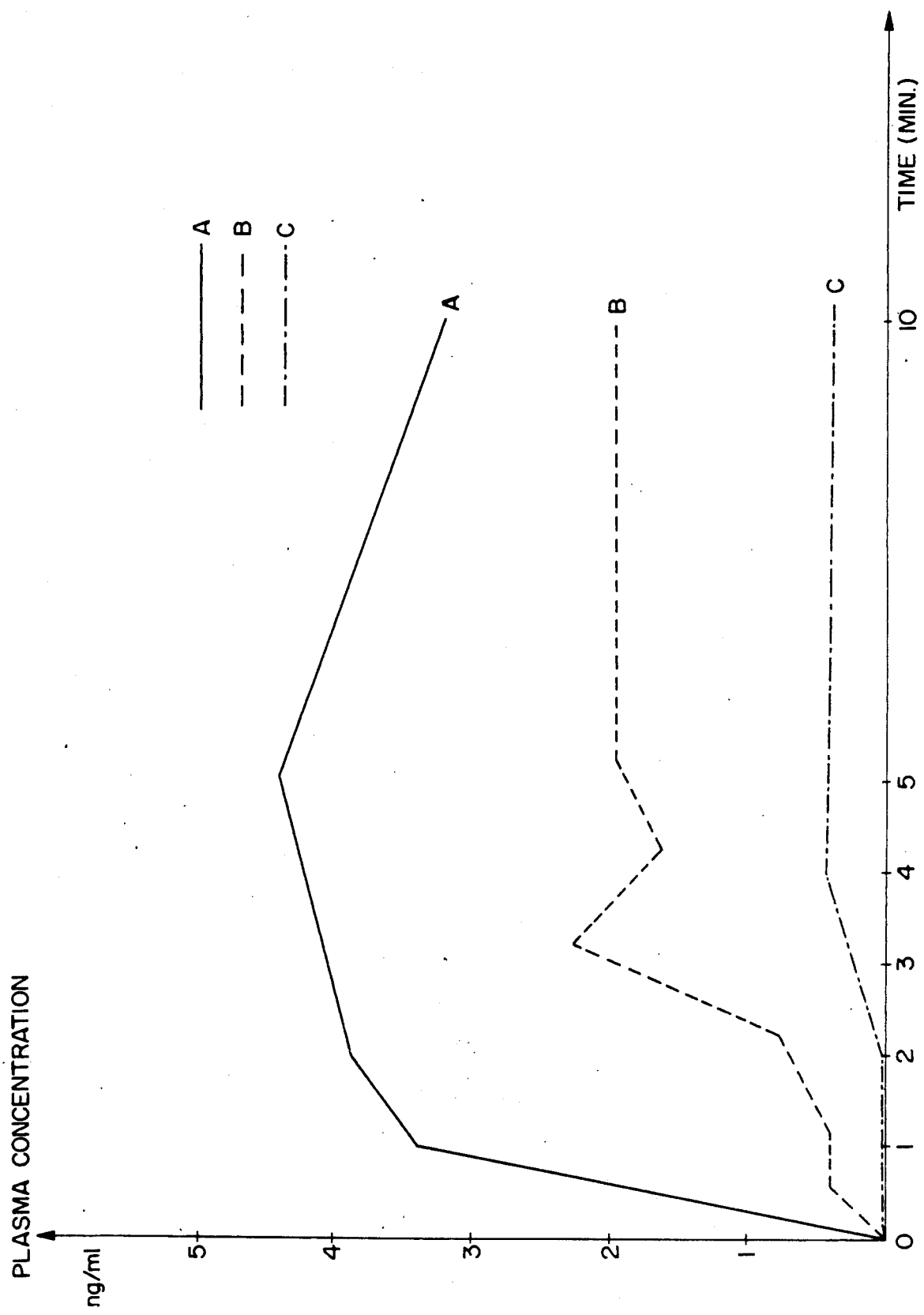

AEROSOL COMPOSITION COMPRISING NITROGLYCERIN AS ACTIVE INGREDIENT

The present invention relates to pharmaceutical compositions comprising nitroglycerin as active ingredient.

The pharmaceutical compositions comprising nitroglycerin as active ingredient have been used as antianginal agents in therapeutical practice for almost a century.

In the British patent specification No. 970,027 aerosol compositions comprising nitroglycerin as active substance are described. According to this specification a quick effect (within 30 seconds) can be achieved only by intravenous injection or inhalation into the lungs, i.e. by pulmonal absorption. The said specification expressively suggests to the man skilled in the art not to use the composition sublingually as this kind of use is considered as obscure, uncontrollable and unverifiable, moreover slower in achieving the desired effect. This British specification regards the application of a propellant gas to be indispensably necessary in order to deliver nitroglycerin to the desired parts of organism, i.e. to the alveoli, and therefore prescribes the suitable limits of the pressure of the propellant gas. In addition, the composition comprises glycols (e.g. propylene glycol, diethylene glycol, etc.) as desensitizing agents. Moreover, 5 to 50% by weight of lower alcohols are added to the composition in order to assure the homogeneity of the system since the glycols used as desensitizing agents do not dissolve in the liquid propellant gases and therefore the alcohol assures the homogeneous liquid phase.

According to the published German patent application (DOS) No. 3,246,081 the propellant gas content of the nitroglycerin spray is increased to 60 to 95% by weight and thus the bioavailability of nitroglycerin is enhanced. According to the tables and curves disclosed in this document the increase of the propellant gas content to the above high value unambiguously increases the plasma concentration and facilitates the establishment of the plasma level corresponding to the appropriate therapeutical effect within a shorter period.

However, the nitroglycerin spray compositions comprising propellant gas suffer from several drawbacks.

It is well known that the halogenated lower alkanes used as propellant gas are harmful for the environment. It is considered that there is relationship between the dangerous decrease of the ozone content of the upper layer of air and the use of high amounts of fluorinated-chlorinated hydrocarbons and therefore the application of propellant gases based on fluorinated-chlorinated aliphatic hydrocarbons is limited in more and more countries.

A further drawback of the propellant gases is that the liquid gases exhibit cooling effect. Especially strong cooling effect is exhibited by "Freon 12" (dichlorodifluoromethane) which is one of the components of the most widely used propellant gas mixture as this component has the lowest boiling point among the usual propellant gases.

A further disadvantages property of the liquid propellant gases in the therapeutic field is the drying effect. The drying of the mucous membrane is unfavourable under all circumstances, but it is especially unfavourable when nitroglycerin compositions are used as the mouth gets dry in case of anginic attacks, that is only a small amount of saliva is formed.

In the "Rote Liste" issued in 1987 nitroglycerin compositions comprising fatty-oily carriers are described. According to the listed compositions $C_{8-12}$, preferably saturated, fatty acid triglycerides (Mygliol ®) are used for this purpose, but low viscosity paraffin oil and natural oils are also applied. According to the art [published German patent application (DOS) No. 3,246,081] these compositions do not assure suitably quick active ingredient release: on the one hand, the plasma level is low and, on the other hand, the peak value is reached within a quite long term (about 4 to 5 minutes). A further disadvantage is that a preservative has to be given to the composition in order to inhibit the decomposition, oxydation of the ingredients and to avoid the composition to become rancid, therefore a further excipient, which does not contribute to the desired therapeutical effect, has to be used in the composition.

The aim of the present invention is to eliminate the drawbacks of the known compositions and to ensure pharmaceutical compositions comprising nitroglycerin as active ingredient without using propellant gases and enabling to reach the appropriate blood level and pharmacodynamic effect within a short time.

The invention is based on the recognition that if nitroglycerin is mixed with a $C_{2-4}$ aliphatic alcohol (component A) and with a polyalkyleneglycol comprising 2 to 3 carbon atoms in the alkylene moiety (component $B_1$) and/or a $C_{2-8}$ alcohol comprising two or three hydroxyl groups (component $B_2$) in the above-identified rates, a propellant gas-free composition can be prepared which, when administered mainly translingually, sublingually or buccally (i.e. through the mucous membrane of the mouth) to the organism, induces a high nitroglycerin blood level within a short time due to its biochemical and biological properties, therefore being especially suitable for the elimination of anginic pain occurring during anginic attacks.

Thus, the aerosol composition according to the invention comprising nitroglycerin as active ingredient and containing no propellant gas comprises 0.1 to 4% by weight of nitroglycerin, 51 to 90% by weight of $C_{2-4}$ aliphatic alcohol (component A), 10 to 49% by weight of a polyalkyleneglycol comprising 2 or 3 carbon atoms in the alkylene moiety (component $B_1$) and/or a $C_{2-8}$ alcohol comprising two or three hydroxyl groups (component $B_2$)

optionally together with one or more pharmaceutically acceptable carriers and/or diluents.

The composition according to the invention is prepared by mixing the components in any sequence and filling the same into bottles.

The nitroglycerin compositions according to the invention can preferably be administered sublingually but they are also suitable for translingual or buccal moreover for external (transdermal) use.

The compositions according to the invention preferably comprise 0.5 to 2.0% by weight, more preferably 0.8 to 1.0% by weight, of nitroglycerin. The component A content of the compositions amounts preferably to 55 to 85% by weight. The compositions comprise preferably 15 to 45% by weight of components $B_1$ and/or $B_2$.

The compositions according to the invention comprise ethyl alcohol, n-propyl alcohol, i-propyl alcohol or straight or branched butyl alcohol, preferably ethyl alcohol as component A.

The compositions comprise polyethylene glycol and/or polypropylene glycol of an average molar weight of 200 to 4000, or the mixture thereof, as component $B_1$.

Polyethylene glycols commercially available as Carbowax®, especially Carbowax 300 of a molar weight of 300, can preferably be used.

The compositions according to the invention can comprise $C_{2-8}$ alcohols having two or three hydroxyl groups, preferably glycerol, propylene glycol or butylene glycol, as component $B_2$.

In addition to nitroglycerin and component A the compositions according to the invention comprise component $B_1$ or component $B_2$ or components $B_1$ and $B_2$.

The preferred composition according to the invention comprises 0.8 to 1.0% by weight of nitroglycerin, 55 to 85% by weight of ethyl alcohol and 15 to 45% by weight of polyethylene glycol, propylene glycol and/or butylene glycol.

The compositions according to the invention can be supplemented with other usual additives. Thus e.g. flavouring agents (e.g. sweeteners such as sorbitol, saccharine, saccharine sodium, etc.) and/or aroma substances (e.g. menthol, peppermint oil, vanilline, anise oil, citrus oil, etc.) and/or antioxidants or light-protective agents (e.g. in case of transparent aerosol bottles) and/or film-forming polymers can be used. The film-forming polymers serve for fixing the composition onto the skin, for inhibiting or decreasing the liquification of the composition on the skin if the composition is used transdermally, while in case of compositions administered through the mouth they decrease the fineness of the spray, the spraying angle and thus the spreading by increasing the viscosity of the composition, thus they inhibit the swallowing of the composition. As film-forming polymer polyvinyl pyrrolidone, carboxymethyl cellulose, hydroxypropyl methyl cellulose, methyl cellulose, ethyl cellulose, alginic acid, propyleneglycol ester, polyvinyl alcohol, carboxyvinyl polymer, etc. can be used.

The compositions can be prepared in a manner known per se in the pharmaceutical industry. According to a preferred embodiment nitroglycerin is dissolved in component A. This operation can be carried out at a temperature of 20° C. or at somewhat lower temperatures. Then component $B_1$ and/or $B_2$ is/are added, thereafter the further additives are admixed. The thus-obtained solution is filtered (e.g. through a sack filter, filter sheet, glass filter or filter candle), then filled into aerosol bottles. The bottles may be made of metal, glass, coated glass or suitable plastic.

One can also proceed by dissolving nitroglycerin in component $B_1$ and/or $B_2$ and the thus-obtained solution is mixed with the alcohol component.

According to a further embodiment of the process of the invention component A is mixed with component $B_1$ and/or $B_2$ and nitroglycerin is dissolved in the mixture thus obtained. The filtration and filling of the solution can be made as described hereinabove.

According to an other embodiment of the process of the invention the nitroglycerin can be adsorbed to a pharmaceutically acceptable substance having suitable specific surface (e.g. lactose) and it can be used in this form. In this case nitroglycerin is dissolved out with the component(s) used for preparing the solution from the carrier and the non-soluble parts of the carrier (e.g. lactose) are filtered out from the solution.

The compositions according to the invention are filled into bottles supplied with appropriate dosing equipment (e.g. valve or inflator). One dose weights 20 to 300 mg, preferably 40 to 100 mg. One dose comprises generally 0.1 to 12 mg, preferably 0.3 to 0.6 mg, of nitroglycerin.

The advantages of the pharmaceutical composition of the invention suitable for transdermal or buccal administration and being free of propellant gases are as follows:

it is free of propellant gas, therefore it is not harmful for the environment;

the alcoholic solution having high alcohol concentration—in contradistinction to the fatty-oily carriers—is directly miscible with saliva, and this results in a better and quicker adsorption of the active ingredient;

the high alcohol concentration results in local hyperaemia, which also leads to a better and quicker resorption;

it can be readily flavoured and precisely dosed.

The favourable properties of the compositions of the invention are verified by clinical tests and blood level tests which are in good accordance with the results of the clinical tests.

1. BLOOD LEVEL TESTS

The plasma concentration of blood samples taken from patients 1, 2, 5, 10 and 15 minutes after the administration of one dose is determined.

The nitroglycerin content of the plasma is determined by high-pressure liquid chromatography (HPLC), using isosorbide dinitrate as inner standard.

The following compositions are used in the test: A: the solution according to Example 1 of the present invention, B: nitroglycerin spray prepared according to Example 1 of the published German patent application No. 3,246,081, C: commercially available nitroglycerin composition comprising 0.9% by weight of nitroglycerin, 27% by weight of neutral oil, 12.4% by weight of liquid paraffin, 2.2% by weight of ether, 0.5% by weight of a flavouring additive and 57.0% by weight of a propellant gas.

The results are summarized in Table I.

Table I

| Time (minute) | Plasma level (ng/ml) | | |
| --- | --- | --- | --- |
| | A | B | C |
| 1 | 3.4 | 0.39 | 0 |
| 2 | 3.9 | 0.66 | 0 |
| 5 | 4.4 | 1.88 | 0.4 |
| 10 | 3.2 | 1.99 | 0.37 |

BRIEF DESCRIPTION OF THE DRAWINGS

FIG. 1 is a diagram wherein the plasma concentration (ng/ml) is plotted against time (minute).

The above results verify that the composition according to the invention ensures the level of 1 ng/ml necessary for the effective elimination of anginal spasms within 20 to 30 seconds. This level could be achieved by using composition B comprising a propellant gas within 2.5 to 3 minutes. Not only the desired plasma concentration can be reached within significantly lower time but even the plasma level is significantly higher.

2. CLINICAL TESTS

The clinical tests were carried out in 8 Hungarian hospitals and institutes and the evaluation of the tests was made with cardiological measurements (objective evaluation) and on the basis of the observations of the patients (subjective evaluation).

Due to the effect of the nitroglycerin spray free from propellant gas, prepared according to Example 1 of the present invention, the a/H ratio (i.e. the estimated final diastolic pressure in the left ventricle) decreases to the normal value, even below 10%, from the initial value of 17.83% within 30 seconds.

The decrease of the a/D ratio being harmfully high at the beginning of the test is already significant after 30 seconds.

A significant increase of the diastolic amplitude index (DATI) can be shown already after 30 seconds.

One minute after administering the spray according to the invention the left ventricle ejection time (LVET) begins to decrease significantly.

During specific ventricle function tests a significant decrease of the calculated left ventricle LDT and filling pressure can be shown within 1 minute.

On the basis of cardiological examinations it can be summarized that the nitroglycerin spray according to the invention decreases the left ventricle filling pressure and the final systolic pressure very quickly, in most cases within 1 minute. The composition exerts its activity even within 30 seconds and the favourable haemodynamic effect is maintained for at least 10 minutes.

Comparative clinical tests were made on 173 patients suffering from angina pectoris. Propellant gas-free spray according to Example 1 and sublingual nitroglycerin tablets were administered to the patients. The composition according to the invention exerted its activity within significantly shorter time, the effect was maintained for about the same time as in the case of the tablet, the frequency of the side-effects corresponded to that of the tablet.

According to our experiments the effect of the spray appears after 1 minute 24 seconds (average value). (The shortest period was 36 seconds, the longest period was 3 minutes 2 seconds.) However, the nitroglycerin tablet exerted its activity after 4 minutes 2 seconds (average value). (The shortest period was 1 minutes 32 seconds, while the longest period was 7 minutes 57 seconds.) Most of the patients considered the propellant gas-free nitroglycerin composition according to the invention better than the tablet and they prefered its use to the use of the tablet.

The invention is further illustrated by the following non-limiting examples.

EXAMPLE 1

A filling solution is prepared with the following composition:

| Component | Weight (g) | % by weight |
| --- | --- | --- |
| Nitroglycerin | 0.08 | 0.80 |
| Ethyl alcohol (98%) | 7.92 | 79.20 |
| Propylene glycol | 2.00 | 20.00 |
| Total weight: | 10.00 | 100.00 |

The nitroglycerin of pharmaceutical quality is dissolved in ethyl alcohol at a temperature of 20° C., then the solution is mixed with propylene glycol. The ready solution is filtered on a metal millipore filter by using a filter sheet of 0.22 μm under vacuum, then it is filled into bottles.

EXAMPLE 2

A filling solution is prepared with the following composition:

| Component | Weight (g) | % by weight |
| --- | --- | --- |
| Nitroglycerin | 0.08 | 0.80 |
| Ethyl alcohol (98%) | 5.50 | 55.00 |
| Carbowax 300 (polyoxyethylene 300) | 4.37 | 43.70 |
| Polyvinyl pyrrolidone | 0.05 | 0.50 |
| Total weight: | 10.00 | 100.00 |

The nitroglycerin of pharmaceutical quality is dissolved in Carbowax 300 at a temperature of 20° C., then the solution is mixed with the solution of polyvinyl pyrrolidone and ethyl alcohol. The solution thus obtained is filtered on a membrane filter sheet (millipore) of 0.22 μm, then it is filled into aerosol bottles.

EXAMPLE 3

A filling solution is prepared with the following composition:

| Component | Weight (g) | % by weight |
| --- | --- | --- |
| Nitroglycerin | 0.20 | 2.00 |
| Butylene glycol | 1.50 | 15.00 |
| Aroma substance | 0.02 | 0.20 |
| Hydroxypropyl methyl cellulose | 0.02 | 0.20 |
| Ethyl alcohol | 8.16 | 82.60 |
| Total weight: | 10.00 | 100.00 |

The composition is prepared as follows:

Nitroglycerin is dissolved in ethyl alcohol and the solution is mixed with butylene glycol, then hydroxypropyl methyl cellulose is dissolved in this solution. The solution thus obtained is filtered as described in Example 1 or 2. In a separate step the aroma substance is dissolved in a small amount of ethyl alcohol, then this solution is added to the filtered solution. Filling into bottles and closing the bottles are carried out as described in Examples 1 or 2.

EXAMPLE 4

A filling solution is prepared with the following composition:

| Component | Weight (g) | % by weight |
| --- | --- | --- |
| Nitroglycerin | 0.10 | 1.00 |
| Ethyl alcohol (98%) | 6.50 | 65.00 |
| Glycerol | 0.50 | 5.00 |
| Carbowax 300 (polyoxyethylene 300) | 2.70 | 27.00 |
| Aroma substance | 0.20 | 2.00 |
| Total weight: | 10.00 | 100.00 |

The ethyl alcoholic solution of nitroglycerin is mixed with glycerol and Carbowax 400. The aroma substance is dissolved in a small amount of ethyl alcohol and added to the filtered solution. Filtration, filling and closing are carried out as described hereinabove.

EXAMPLE 5

A filling solution of the following composition is prepared according to Example 1:

| Component | Weight (g) | % by weight |
| --- | --- | --- |
| Nitroglycerin | 0.01 | 0.10 |
| Ethyl alcohol (98%) | 8.95 | 89.50 |

-continued

| Component | Weight (g) | % by weight |
| --- | --- | --- |
| Polyethylene glycol 400 | 0.60 | 6.00 |
| Propylene glycol | 0.40 | 4.00 |
| Aroma substance | 0.04 | 0.40 |
| Total weight: | 10.00 | 100.00 |

EXAMPLE 6

A filling solution of the following composition is prepared according to Example 1:

| Component | Weight (g) | % by weight |
| --- | --- | --- |
| Nitroglycerin | 0.40 | 4.00 |
| n-Butyl alcohol | 5.10 | 51.00 |
| Polyethylene glycol 200 | 4.00 | 40.00 |
| Sorbitol | 0.45 | 4.50 |
| Aroma substance | 0.05 | 0.50 |
| Total weight: | 10.00 | 100.00 |

EXAMPLE 7

A filling solution of the following composition is prepared according to Example 1:

| Component | Weight (g) | % by weight |
| --- | --- | --- |
| Nitroglycerin | 0.01 | 0.10 |
| Ethyl alcohol (98%) | 9.00 | 90.00 |
| Propylene glycol | 0.99 | 9.90 |
| Total weight: | 10.00 | 100.00 |

We claim:

1. An aerosol composition free of propellant gas which comprises 0.1 to 4% by weight of nitroglycerin, 51 to 90% by weight of a $C_{2-4}$ aliphatic alcohol (component A), and 10 to 49% by weight of a polyalkyleneglycol containing 2 or 3 carbon atoms in the alkylene moiety (component $B_1$) and/or a $C_{2-8}$ alcohol containing two or three hydroxyl groups (component $B_2$)

optionally together with one or more pharmaceutically acceptable carriers and/or diluents.

2. A composition as defined in claim 1, wherein component A is ethyl alcohol.

3. A composition as defined in claim 1, wherein polyethylene glycol or polypropylene glycol is present as component $B_1$.

4. A composition as defined in claim 2, wherein glycerol, propylene glycol or butylene glycol is present as component $B_2$.

5. A composition as claimed in claim 1, which comprises 0.8 to 1.0% by weight of nitroglycerin, 55 to 85% by weight of ethyl alcohol and 15 to 45% by weight of polyethylene glycol, propylene glycol and/or butylene glycol.

6. A process for the preparation of aerosol compositions free of propellant gas containing nitroglycerin as active ingredient, which comprises mixing 0.1 to 4% by weight of nitroglycerin, 51 to 90% by weight of a $C_{2-4}$ aliphatic alcohol (component A), and 10 to 49% by weight of a polyalkyleneglycol containing 2 or 3 carbon atoms in the alkylene moiety (component $B_1$) and/or a $C_{2-8}$ alcohol containing two or three hydroxyl groups (component $B_2$)

optionally together with one or more pharmaceutically acceptable carriers and/or diluents in any sequence and filling the thus-obtained solution into bottle.

7. A process as defined in claim 6, wherein component A is ethyl alcohol.

8. A process as defined in claim 6, wherein polyethylene glycol or polypropylene glycol is present as component $B_1$.

9. A process as defined in claim 6, wherein glycerol, propylene glycol or butylene glycol is present as component $B_2$.

10. A process as defined in claim 6, wherein the composition contains 0.8 to 1.0% by weight of nitroglycerin, 55 to 85% by weight of ethyl alcohol and 15 to 45% by weight of polyethylene glycol, propylene glycol and/or butylene glycol.

11. A process as defined in claim 6, wherein nitroglycerine is dissolved in component A, and then the solution thus obtained is mixed with component $B_1$ and/or $B_2$.

12. A process as defined in claim 6, wherein nitroglycerine is dissolved in component $B_1$ and/or $B_2$, and then the solution thus obtained is mixed with component A.

13. A process as defined in claim 6, wherein nitroglycerin is dissolved in the solution of component A and component $B_1$ and/or $B_2$.

* * * * *